United States Patent

Rossini et al.

Patent Number: 6,107,535
Date of Patent: Aug. 22, 2000

[54] PROCESS FOR REMOVING NITROGENATED AND SULFURATED CONTAMINANTS FROM HYDROCARBON STREAMS

[75] Inventors: Stefano Rossini, Milan; Valerio Piccoli, Monza-Milan, both of Italy

[73] Assignee: Snamprogette S.p.A., San Donato Milanese, Italy

[21] Appl. No.: 09/147,162

[22] PCT Filed: Apr. 16, 1997

[86] PCT No.: PCT/EP97/01993

§ 371 Date: Oct. 21, 1998

§ 102(e) Date: Oct. 21, 1998

[87] PCT Pub. No.: WO97/39994

PCT Pub. Date: Oct. 30, 1997

[30] Foreign Application Priority Data

Apr. 22, 1996 [IT] Italy .................................. MI96A0772

[51] Int. Cl.⁷ .............................. C07C 7/12; C10G 25/00; C10G 25/12

[52] U.S. Cl. .......................... 585/823; 585/820; 585/826; 208/208 R; 208/254 R; 208/307; 208/245; 208/299; 208/305

[58] Field of Search ........................... 208/208 R, 254 R, 208/307, 245, 299, 305; 585/820, 823, 826

[56] References Cited

U.S. PATENT DOCUMENTS

| | | | |
|---|---|---|---|
| 3,620,969 | 11/1971 | Turnock | 208/245 |
| 4,329,222 | 5/1982 | Habeed | 208/254 R |
| 4,343,693 | 8/1982 | Holland et al. | 208/244 |
| 4,529,504 | 7/1985 | Poirier et al. | 208/254 R |
| 4,830,733 | 5/1989 | Nagji et al. | 208/208 R |
| 4,846,962 | 7/1989 | Yao | 208/301 |
| 5,888,402 | 3/1999 | Hommeltoft et al. | 210/690 |
| 5,942,650 | 8/1999 | Gajda | 585/448 |

*Primary Examiner*—Walter D. Griffin
*Assistant Examiner*—Tam M. Nguyen
*Attorney, Agent, or Firm*—Oblon, Spivak, McClelland, Maier & Neustadt, P.C.

[57] ABSTRACT

A process for selectively removing nitrogenated and/or sulfurated contaminants from streams prevalently containing hydrocarbons with from 3 to 8 crbon atoms characterized in that it comprises an adsorption step wherein said contaminants are adsorbed by an adsorbent essentially consisting of silica gel at a temperature of between 0 and 150° C. and at a pressure of between 1 and 20 atm and a regeneration step to remove the adsorbed substances by thermal treatment in a stream of insert gas carried out at a temperature of between 100 and 200° C.

7 Claims, No Drawings

PROCESS FOR REMOVING NITROGENATED AND SULFURATED CONTAMINANTS FROM HYDROCARBON STREAMS

The present invention relates to a process for selectively removing nitrogenated and/or sulfurated contaminants from streams prevalently containing hydrocarbons with from 3 to 8 carbon atoms.

Many refinery and petroichemical processes are sensitive to the presence of nitrogenated and sulfurated compounds, as they more or less seriously deactivate the catalytic systems. The nitrogenated compounds are generally of a basic nature and consequently preferably, but not exclusively, interfere with acid-catalyst processes.

The removal of heteroatoms such as nitrogen and sulfur is generally an extremely significant aspect in the treatment of the raw material, with respect to both the quality of the cuts obtained and the formation of oxides, especially nitrogen, in combustion when this species enters the carburating pools.

The removal of nitrogen is generally carried out hydrogenating treatment under strict conditions of temperature and pressure, especially for cuts to be sent to hydrocracking and/or reforming. Sulfur is also preferably removed by hydrogenation.

It is not generally considered useful or convient to remove contaminated products, especially nitrogenated, from light cuts. It has been observed however that $C_4$ and $C_5$ fractions coming from an FCC unit can contain nitriles, typically acetonitrile and propionitrile, extremely harmful for catalytic systems of both etherification reactions of iso-olefins with alcohols to give the respective ethers (MTBE, ETBE, TAME, TAEE) and skeleton isomerization reactions of olefins, from linear to branched. The role of the ethers is to bring oxygen and possibly improve the octanic properties as well as to reduce the olefin degree of the gasolines mainly with the aim of their reformulation (U.S. Clean Air Act Amendments, Publication 101-549-Nov. 15, 1990).

It is therefore of primary importance to be able to eliminate the nitriles, generally present at very low levels measurable in ppm, in the cuts which are used in the above technologies.

This removal can essentially take place in two ways:
a) by processes which necessitate a chemical transformation of the —CN reactive group of the molecul;
b) by adsorption on suitable material.

The present art provides disclosures for both procedures.

For procedure (a) U.S. Pat. No. 5,414,183 claims the removal of nitriles, by hydrolysis, by putting the hydrocarbon stream in contact with an alkaline solution of NaOH at temperatures of about 100° C. and a pressure of 14 atm in a static mixer. The total removal of the nitrogen is obtained only with relatively long contact times.

Method (a) is limited to those compounds having a functional CN group and it is therefore necessary to resort to other separation techniques when other contaminants are present, whether they be nitrogenated or not.

For procedure (b) the material must selectively remove the contaminants with respect to the stream in which they are inserted.

A first disclosure is provided in U.S. Pat. No. 4,831,206 where the impurities containing sulfur and nitrogen of a hydrocarbon stream are removed in two steps: in the first, there is the hydrogenation of these substances to hydrogen sulfide and ammonia, which are then adsorbed in the second step by putting the outgoing stream in contact with a material selected from zeolite 4A, 5A and clinoptilolite.

This adsorption can take place in both liquid phase and gas phase, with temperatures of between 150 and 290° C. and adsorption periods of between 0.2 and 2 hours, the pressure being determined by the process downstream (isomerization, reforming, etc.) and in any case between 100 and 400 psig. The adsorption beds are regenerated before there is, by saturation of the bed itself, the release of hydrogen sulfide and ammonia. The same disclosure is provided in U.S. Pat. No. 4,831,207 which also claims zeolite 13X as adsorbing agent, whereas the configuration of the plant comprises two adsorption beds, for ammonia and hydrogen sulfide, one being for adsorption, the other for desorption. It has been observed that in both cases a hydrogenation step is necessary to reduce the nitrogenated and sulfurated compounds present to hydrogen sulfide and ammonia.

U.S. Pat. No. 5,120,881 claims a process wherein, before an etherification step of isobutene to give MTBE, the compounds containing nitrogen-nitriles, amine, amide, ammonia and mixtures—and possibly dialkylsulfides are adsorbed on zeolites, such as X, Y, L, Beta and mordenite, the preferred being zeolite X in sodic form. The sorption temperature deduced from the examples is 35° C.

A process has been surprisingly found using a material which combines high adsorbing capacity (moleules retained per unit of adsorbent mass under equilibrium conditions) for nitrogenated and sulfurated compounds with a high adsorption rate of these moleules (molecules adsorbed per unit of time), at the same time allowing the material to be easily and completely regenerated. This latter aspect, although not indicated in the art mentioned, is of fundamental importance for applying the method on an industrial scale.

The process for selectively removing nitrogenated and/or sulfurated contaminants from streams prevalently containing hydrocarbons with from 3 to 8 carbon atoms, of the present invention, is characterized in that it comprises an adsorption step wherein said contaminants are adsorbed by means of an adsorbent essentially consisting of silica gel, at a temperature of between 0 and 150° C. and a pressure of between 1 and 20 atm, and a regeneration step for removing the adsorbed substances by means of thermal treatment in a stream of inert gas, carried out at a temperature of between 100 and 200° C.

The inert gas used in the thermal treatment can be selected from the gases normally used for carrying out these regenerations, such as nitrogen, helium, steam, flue gas, air, etc.

The silica gel used can have a surface area preferably higher than 300 $m^2/g$, more preferably higher than 400 $m^2/g$, and a porous volume preferably of between 0.38 and 1.75 ml/g.

The contaminants which are normally present in the hydrocarbon streams are, among the nitrogenated ones, nitriles, such as acetonitrile or propionitrile, amines, such as alkylamines (propylamine, butylamine, ammonia, diethylamine, ethanolamine, etc.), among the sulfurated ones, dialkylsulfides such as methylethylsulfide, mercaptans, such as n-butylmercaptan, alkylthiophenes, such as thiophene.

The hydrocarbon streams under consideration can typically contain paraffins, olefins or diolefins, prevalently with from 3 to 8 carbon atoms and normally contain not more than a few hundred ppm of nitrogenated compounds and less than 100 ppm of sulfurated compounds. This however does not prevent the use of the process claimed herein for streams with a much higher content of contaminants making it necessary to include more recycles to obtain the removal of these nitrogenated and/or sulfurated substances.

In addition this material can contain other components without jeopardizing the specific behaviour described therein.

For example commercial silica gel can contain several impurities, such as for example $Na^+$, $Ca^{2+}$, $Fe^{3+}$, $SO_4^{2-}$ and $Cl^-$, on a level of several hundred ppm, or modifiers for specific uses, such as for example $Co^{2-}$, or it can have the nature of a cogel and contain for example $Al^{3+}$, $Zr^{4+}$, $Ti^{4+}$, $Mg^{2+}$.

A very interesting aspect of this material is that it has a moderate acidity under the applicative conditions, which above all is not sufficient to cause undesired polymerization or isomerization reactions in the hydrocarbon streams, mainly olefinic, to be treated and which is not sufficient to react with the contaminant, which would make it difficult to regenerate.

Another peculiar and surprising aspect of this material is that, if a stream is to be treated which contemporaneously contains paraffins and olefins, it does not preferentially adsorb the olefinic component, unlike adsorbing materials based on zeolites, such as zeolite 13X, which tends to preferentially adsorb the olefinic component and does not therefore alter the composition of the hydrocarbon stream which is used.

A further aspect which is equally important as those already mentioned consists in the capacity of silica gel to selectively adsorb contaminants from the hydrocarbon streams both in gaseous and liquid phases.

The removal of the contaminants is generally a cyclic operation which involves an adsorption step and a regeneration step of the material (desorption of the adsorbed contaminant). The times for each step of the cycle are strictly correlated to the operating conditions in adsorption phase, such as for example the quantity of contaminant to be removed, the space velocity, the operating pressure and temperature. It can be easily deduced that by increasing the loading of the contaminant and the space velocity, the times of the adsorption phase are shortened, as the saturation of the material is more rapidly reached, or by increasing the temperature the adsorbing capacity decreases.

Silica gel has an adsorption capacity for nitriles (and for other basic substances—for example n-propyl-amine) which can even reach 13–15% by weight, if they are in contact with a hydrocarbon stream which contains several thousand ppm of them.

The following examples, which do not limit the scope of the invention, illustrate the experimental methods used in the examples relating to the application of silica gel for the removal of nitrogenated compounds (nitriles, amines) or sulfurated compounds (mercaptans, dialkylsulfides, thiophene).

EXAMPLES

Two types of experiments were carried out:
tests in batch
tests on stream.

The adsorbing capacities (weight of contaminant/weight of adsorbing solid×100) of various materials with respect to various contaminants were evaluated by the tests in batch.

The tests in batch allowed both the suitability of a given material used under flow conditions (which are more interesting for practical application) and the maximum period of use for said material to be determined.

The regenerability of the materials was verified by subjecting the exhausted material to thermal treatment in a stream of inert gas (air, nitrogen, etc.).

In short it was asserted that silica gel has the capacity of selectively adsorbing contaminants (nitrogenated and sulfurated) from hydrocarbon streams both in gaseous phase and in liquid phase. It is also mechanically and chemically stable under operating conditions and can be easily regenerated without any deterioration in its efficiency after repeated adsorption-regeneration cycles.

Example 1

Evaluation of the Adsorbing Capacity of Various Materials with Respect to Propionitrile (in batch)

Tests in batch were carried out to evaluate the adsorbing capacity of various materials with respect to propionitrile (selected as a general representative of nitriles).

9.9 g of a hydrocarbon mixture containing $C_5$ olefins and paraffins in a ratio 1:2 and containing 5800 ppm of PrCN is put in contact with 0.5 g of the material under examination previously dried at 200° C. for about 2 h. The whole mixture is placed in a closed pyrex container, at room temperature, 23° C., and a pressure equal to the vapour pressure of the mixture at the above temperature. The evolution of the composition of the liquid is analyzed by gaschromatography. The data obtained allow the quantity of PrCN adsorbed by the solid under examination to be calculated.

Table 1 shows the results of the screening on various materials.

From this data the following conclusions can be drawn.

In confirmation of what is mentioned above, it is served that it is preferable to use silica gel with high surface area.

From these data it seems that the high surface area is an essential requisite for guaranteeing adsorbing efficiency.

The surface area however is generally not sufficient, in fact a comparison between silica gel with a high surface area and active carbons (both characterized by high surface areas) distinctly favours the former.

Another group of interesting materials is that of zeolites, especially in sodic form, already known in patent literature. In this group zeolite 13X is the most efficient.

In the group of zeolitic materials the limited efficiency of silicalite (particular type of zeolite which does not contain aluminium, unless as an impurity) with respect to zeolites, shows that the presence of electrostatic charges seems to be determinant. The presence of acid centres in a zeolite is not an asset, in fact zeolites in sodic form are more efficient (HY Zeolite<LaY Zeolite<NaY Zeolite).

Example 2

Adsorption of PrCN from a Mixture of $C_8$ Olefins and Paraffins (in batch)

9.98 g of a mixture containing $C_8$ olefins and paraffins with 14330 ppm of PrCN, whose composition is shown in table IIa, are put in contact with 0.516 g of silica gel, in crystals having about 3 mm of equivalent diameter, previously dried at 200° C. for about 2 h. The mixture in contact with the silica gel is placed in a closed pyrex container, at room temperature, 23° C., and a pressure equal to the vapour pressure of the mixture. The evolution of the concentration of the liquid in time is analyzed by gaschromatography. The data obtained enable the quantity of PrCN adsorbed by the silica gel to be calculated. The results are shown in table IIb.

After about 4 hours an equilibrium situation is reached. Each g of anhydrous silica gel under these conditions of concentration, temperature, pressure is capable of adsorbing 0.14 g of PrCN. The adsorption is selective. The ratio isooctane/1 octene of the initial hydrocarbon mixture is equal to 1.02 (weight/weight) and remains unaltered in the liquid mixture at equilibrium.

Example 3
Adsorption of nBuSH from a Mixture of $C_5$ Olefins and Paraffins (in batch)

9.96 g of a mixture containing $C_5$ olefins and paraffins and 4740 ppm of butyl mercaptan (nBuSH), whose composition is shown in table IIIa, are put in contact with 0.510 g of silica gel, in crystals having about 3 mm of equivalent diameter, previously dried at 200° C. for about 2 h. The mixture in contact with the silica gel is placed in a closed pyrex container, at room temperature, 23° C., and a pressure equal to the vapour pressure of the mixture. The evolution of the concentration of the liquid in time is analyzed by gaschromatography. The data obtained enable the quantity of nBuSH adsorbed by the silica gel to be calculated. The results are shown in table IIIb.

After about 24 hours an equilibrium situation is reached. Each g of anhydrous silica gel under these conditions of concentration, temperature, pressure is capable of adsorbing 0.03 g of nBuSH. The adsorption is selective.

Example 4
Adsorption of $nPrNH_2$ from a Mixture of $C_5$ Olefins and Paraffins (in batch)

9.97 g of a mixture containing $C_5$ olefins and paraffins and 6190 ppm of $nPrNH_2$, whose composition is shown in table IVa, are put in contact with 0.516 g of silica gel, in crystals having about 3 mm of equivalent diameter, previously dried at 200° C. for about 2 h. The mixture in contact with the silica gel is placed in a closed pyrex container, at room temperature, 23° C., and a pressure equal to the vapour pressure of the mixture. The evolution of the concentration of the liquid in time is analyzed by gaschromatography. The data obtained enable the quantity of $nPrNH_2$ adsorbed by the silica gel to be calculated. The results are shown in table IVb.

After about 24 hours an equilibrium situation is reached. Each g of anhydrous silica gel under these conditions of concentration, temperature, pressure is capable of adsorbing 0.09 g of $nPrNH_2$. The adsorption is selective.

Example 5
Adsorption of AcCN from a Mixture of Butenes (on stream)

A comparative test is carried out between the capacity of adsorbing AcCN in gas phase of silica gel and a commercial adsorbent (TSN-1 Sud Chemie) available for the same use.

The adsorbent bed is situated upstream of a reactor for the skeleton isomerization of butenes, at room temperature, atmospheric pressure. The mixture of butenes containing AcCN, whose composition is shown in table Va, passes through the adsorbent bed at WHSV=5.

The composition of the gas leaving the AcCN trap is analyzed by gaschromatography. The results obtained for the two materials compared, in relation to the time, are summarized in table Vb. It is evident how with the same time the adsorption yield and the adsorbing capacity of silica gel are higher than those of the TSN-1.

Example 6
Adsorption of PrCN from a Mixture of Pentenes (on stream)

The adsorption bed consists of 0.205 g of silica gel, previously dried at 150° C. and granulated at 25–60 mesh, charged into a tubular pyrex reaction with an internal diameter of 2 mm. The reactor is fed by means of a dosage pump for HPLC and is maintained at room temperature (22° C.) and at a pressure of 2.4 atms. The feeding consists of a mixture of $C_5$ paraffins and olefins contaminated by 144 ppm of PrCN, the composition is indicatd in table VIa. Downstream of the reactor it is possible to completely collect the liquid, which is weighed to accurately determine the WHSV used and analyzed by gaschromatography to evaluate the presence of contaminated products to be eliminated.

The results obtained are summarized in table VIb.

It is evident how silica gel maintains an adsorption yield of 100% even at very high WHSV values.

The ratio pentene-1/isopentane of the initial hydrocarbon mixture is equal to 1:2 (weight/weight) and remains unaltered in the liquid mixture at equilibrium.

Example 7
Adsorption of Propionitrile from a $C_5$ Hydrocarbon Mixture in Liquid Phase (on stream).

0.5 g of solid rae charged into a tubular reactor. A mixture of olefins and paraffins in liquid phase containing about 45 ppm of propionitrile is passed through the solid. The composition of the mixture leaving the reactor is determined by gaschromatography.

Table VII shows the results relating to the silica gel with a high surface area.

The test conditions are:

Solid charge: 0.5 g

Solid particle size: 40–60 MESH

WHSV: 5 $H^{-1}$

PrCN: 45 ppm

Temperature: 23° C.

Pressure: 2.3 atm

Example 8
Regeneration of the Silica Gel

The sample of material resulting from the test described in example 7, thus exhausted, is placed in a tubular reactor in a stream of inert gas (He: 10 cc/min) and brought in 1 hour from 25 to 200° C. The composition of the effluent gas is analyzed and quantified by means of a gas-chromatograph connected on-line. Table VIII shows the results of the regeneration of a sample silica gel with a high surface area.

The test conditions are:

Temperature: as indicated in the table

He stream: 10 cc/min

Solid charge: 0.5 g

The data in the table show a different behaviour between water and propionitrile, water being more easily released than propionitrile.

Under test conditions the regeneration can therefore be completed at 200° C. if it is prolonged for a sufficient time.

The material regenerated as described above and subjected to a new adsorption cycle in continuous does not indicate any deterioration in efficiency in removing propionitrile as illustrated in table 1.

TABLE 1

Adsorption of propionitrile on various materials:
tests in batch
(T = 23° C.; P = 1 atm; PrCN = 5800 ppm)

| | PrCN adsorbed (100 * g PrCN/g solid) Time (min) | | | | | |
|---|---|---|---|---|---|---|
| Material | 3 | 10 | 60 | 120 | 240 | equil. |
| Silica gel (600 m²/g) | 7.3 | 7.9 | 8.6 | 8.7 | 8.8 | 8.8 |
| Silica-gel Grace (200 m²/g) | 2 | 2.5 | 4 | 4.2 | 4.2 | 4.2 |
| Silica-alumina Grace (400 m²/g) | 5 | 6 | 6.8 | 6.9 | 7 | 7 |

TABLE 1-continued

Adsorption of propionitrile on various materials: tests in batch
(T = 23° C.; P = 1 atm; PrCN = 5800 ppm)

PrCN adsorbed (100 * g PrCN/g solid)
Time (min)

| Material | 3 | 10 | 60 | 120 | 240 | equil. |
|---|---|---|---|---|---|---|
| Active carbon (1000 m²/g) | 1 | 1.4 | 2.7 | 3.5 | 3.6 | 3.7 |
| Silicalite | 4.8 | 5.5 | 6.5 | 6.6 | 6.6 | 6.6 |
| Zeolite 13X Na | 7.9 | 8.4 | 9.7 | 10.2 | 12 | 12 |
| Zeolite HY | 4 | 5.6 | 7 | 8.1 | 9.5 | 10 |
| Zeolite LaY | 7 | 8 | 8.8 | 9.5 | 10.2 | 10.4 |
| Zeolite NaY | 6.7 | 7.5 | 8.4 | 9.4 | 10.7 | 10.7 |
| Silica Gel regenerated (600 m²/g) | 7.2 | 7.9 | 8.4 | 8.4 | 8.5 | 8.6 |

TABLE IIa

Composition initial mixture

| component | (weight %) |
|---|---|
| PrCN | 1.43 |
| iso-octane | 49.17 |
| 1-octene | 48.07 |
| mix HC(C$_{7-8}$) | 0.95 |
| mix HC (C$_{8+}$) | 0.38 |

TABLE IIb

PrCN adsorbed

| t(min) | Yield ads (%) | PrCN ads(g/g %)^ |
|---|---|---|
| 5 | 16.70 | 4.6 |
| 240 | 48.7 | 13.6 |
| 1350 | 49.8 | 13.9 |

^ = g of PrCN/g anhydrous silica gel * 100

TABLE IIIa

Composition initial mixture

| component | (weight %) |
|---|---|
| BuSH | 0.473 |
| isobutane | 0.011 |
| n-butane | 0.006 |
| neo-pentane | 0.019 |
| 3Me1-butene | 0.006 |
| iso-pentane | 68.839 |
| 1-pentene | 29.972 |
| 2Me-1-butene | 0.120 |
| n-pentane | 0.170 |
| isoprene | 0.003 |
| 2-pentene-trans | 0.318 |
| 2-pentene-cis | 0.027 |
| 2Me-2-butene | 0.029 |
| C$_{5+}$ hydrocarbons | 0.006 |

TABLE IIIb nBuSH adsorbed

| t(min) | Yield ads(%) | nBuSH ads (g/g %)^ |
|---|---|---|
| 7 | 5.2 | 0.5 |
| 320 | 17.7 | 1.6 |

TABLE IIIb-continued nBuSH adsorbed

| t(min) | Yield ads(%) | nBuSH ads (g/g %)^ |
|---|---|---|
| 1320 | 30.9 | 2.8 |
| 1740 | 34.4 | 3.2 |

^ = g of nBuSH/g anhydrous silica gel * 100

TABLE IVa

Composition initial mixture

| component | (weight %) |
|---|---|
| nPrNH$_2$ | 0.619 |
| isobutane | 0.011 |
| n-butane | 0.006 |
| neo-pentane | 0.018 |
| 3Me1-butene | 0.006 |
| iso-pentane | 68.775 |
| 1-pentene | 29.885 |
| 2Me-1-butene | 0.120 |
| n-pentane | 0.170 |
| isoprene | 0.003 |
| 2-pentene-trans | 0.318 |
| 2-pentene-cis | 0.027 |
| 2Me-2-butene | 0.027 |
| C$_{5+}$ hydrocarbons | 0.014 |

TABLE IVb nPrNH$_2$ adsorbed

| t(min) | Yield ads(%) | nPrNH$_2$ ads (g/g %)^ |
|---|---|---|
| 5 | 19.7 | 2.3 |
| 180 | 34.7 | 4.2 |
| 1740 | 73.2 | 8.8 |
| 1740 | 34.4 | 3.2 |

^ = g of nPrNH$_2$/g anhydrous silica gel * 100

TABLE Va

Composition initial mixture

| component | (weight %) |
|---|---|
| 1-butene | 79.957 |
| iso-butane | 19.950 |
| AcCN | 0.043 |
| H$_2$O | 0.050 |

TABLE Vb

Adsorption AcCN from mixture of butenes in gas phase

| | TSN-1 | | Silica gel | |
|---|---|---|---|---|
| t(h) | AcCN$_{out}$ ppm | AcCN$_{ads}$ (g/g %) | AcCN$_{out}$ (ppm) | AcCN$_{ads}$ (g/g %) |
| 0.08 | 0 | 0.02 | 0 | 0.02 |
| 0.5 | 12 | 0.11 | 0 | 0.11 |
| 1 | 41 | 0.20 | 0 | 0.22 |
| 2 | 106 | 0.36 | 0 | 0.43 |
| 3 | 169 | 0.50 | 0 | 0.65 |
| 5 | 280 | 0.65 | 0 | 1.08 |
| 6 | 351 | 0.68 | 0 | 1.29 |
| 6.7 | 363 | 0.71 | 0 | 1.44 |
| 8 | | | 0 | 1.72 |

TABLE Vb-continued

Adsorption AcCN from mixture of butenes in gas phase

| | TSN-1 | | Silica gel | |
|---|---|---|---|---|
| t(h) | AcCN$_{out}$ ppm | AcCN$_{ads}$ (g/g %) | AcCN$_{out}$ (ppm) | AcCN$_{ads}$ (g/g %)^ |
| 9 | | | 0 | 1.93 |
| 10 | | | 107 | 2.09 |

^ = g of AcCN/g of adsorbent * 100

TABLE VIa

Composition initial mixture

| component | (weight %) |
|---|---|
| 1 pentene | 29.786 |
| iso-pentane | 69.885 |
| PrCN | 0.014 |
| other hydrocarbons | 0.315 |

TABLE VIb

PrCN adsorbed

| t(min) | WHSVPrCNads (%) | PrCNads (g/g %)^ |
|---|---|---|
| 151 | 9.54 100.0 | 0.40 |
| 242 | 19.08 100.0 | 0.75 |
| 312 | 38.16 100.0 | 1.11 |
| 449 | 38.16 100.0 | 2.23 |
| 598 | 21.89 100.0 | 2.94 |

^ 0 g of PrCN/g of adsorbent * 100

TABLE VII

Tests on stream silica gel (600 m²/g)

| time (h) | PrCN$_{out}$ (ppm) | PrCN$_{adsorbed}$ (weight %) |
|---|---|---|
| 0 | 0 | 0 |
| 20 | 0 | 0.45 |
| 40 | 0 | 0.9 |
| 60 | 0 | 1.37 |
| 80 | 0 | 1.82 |
| 100 | 8 | 2.16 |
| 110 | 45 | 2.2 |

TABLE VIII

Regeneration of silica gel (600 m²/g)

| time (min) | Temperature (° C.) | Pr-CN arbitrary units | H$_2$O arbitrary units |
|---|---|---|---|
| 10 | 37 | 210 | 289.8 |
| 15 | 60 | 225 | 894.7 |
| 20 | 70 | 344 | 1268.6 |
| 25 | 80 | 488 | 1789.3 |
| 30 | 93 | 696 | 2488.9 |
| 35 | 108 | 899 | 2993.2 |
| 40 | 123 | 1172 | 2916.5 |
| 45 | 138 | 1671 | 2189.5 |
| 50 | 153 | 2424 | 1394.1 |
| 55 | 167 | 3174 | 717.4 |
| 60 | 181 | 3543 | 406.6 |
| 65 | 196 | 3120 | 3175 |
| 70 | 204 | 1875 | 223 |
| 75 | 203 | 941 | 157.6 |
| 80 | 203 | 464 | 154.7 |
| 85 | 203 | 341 | 138.8 |
| 90 | 203 | 248 | 136.6 |
| 100 | 203 | 200 | 136.7 |

What is claimed is:

1. A process for selectively removing nitrogenated and/or sulfurated contaminants from streams prevalently containing hydrocarbons with from 3 to 8 carbon atoms characterized in that it comprises an adsorption step wherein said contaminants are adsorbed by an adsorbent consisting essentially of silica gel at a temperature of between 0 and 150° C. and at a pressure of between 1 and 20 atm, and a regeneration step to remove the adsorbed substances by thermal treatment in a stream of inert gas carried out at a temperature of between 100 and 200° C., wherein said silica gel has a surface area greater than 300 m²/g.

2. The process according to claim 1 wherein the silica gel has a surface area greater than 400 m²/g.

3. The process according to claim 1 wherein the silica gel has a porous volume of between 0.38 and 1.75 ml/g.

4. The process according to claim 1 wherein the inert gas in the regeneration step is selected from nitrogen, helium, flue gas, air or steam.

5. The process according to claim 1 wherein the contaminants are adsorbed in gaseous phase.

6. The process according to claim 1 wherein the contaminants are adsorbed in liquid phase.

7. The process according to claim 1, wherein the contaminants are nitrogenated contaminants.

* * * * *

UNITED STATES PATENT AND TRADEMARK OFFICE
CERTIFICATE OF CORRECTION

PATENT NO. : 6,107,535

DATED : August 22, 2000

INVENTOR(S): Stefano ROSSINI, et al.

It is certified that an error appears in the above-identified patent and that said Letters Patent is hereby corrected as shown below:

On the Title Page, Item [ 73] the Assignee is misspelled. It should read as follows:

[73] Assignee: Snamprogetti S.p.A., San Donato Milanese, Italy

Signed and Sealed this

Seventeenth Day of April, 2001

*Attest:*

NICHOLAS P. GODICI

*Attesting Officer*     *Acting Director of the United States Patent and Trademark Office*